United States Patent
Haug et al.

(10) Patent No.: US 7,427,769 B2
(45) Date of Patent: Sep. 23, 2008

(54) IMAGE CARRIER FOR STORING X-RAY INFORMATION, AND A SYSTEM AND METHOD FOR PROCESSING AN IMAGE CARRIER

(75) Inventors: Werner Haug, München (DE); Walter Encke, Gilching (DE); Oskar Hujer, Jetzendorf (DE)

(73) Assignee: Afga-Gevaert HealthCare GmbH, Leverkusen (DE)

( * ) Notice: Subject to any disclaimer, the term of this patent is extended or adjusted under 35 U.S.C. 154(b) by 113 days.

(21) Appl. No.: 11/010,658

(22) Filed: Dec. 9, 2004

(65) Prior Publication Data

US 2005/0133745 A1    Jun. 23, 2005

(30) Foreign Application Priority Data

Dec. 17, 2003    (EP) ................... 03104749

(51) Int. Cl.
  *G03B 42/02* (2006.01)
(52) U.S. Cl. ............. 250/581; 250/484.4; 250/252.1; 378/165
(58) Field of Classification Search ........... 250/581, 250/484.4; 378/165; 713/185; 343/906
See application file for complete search history.

(56) References Cited

U.S. PATENT DOCUMENTS

| | | | |
|---|---|---|---|
| 4,320,296 A | | 3/1982 | Ishida et al. |
| 4,498,005 A | | 2/1985 | Oono et al. |
| 4,739,480 A | | 4/1988 | Oono et al. |
| 4,960,994 A | * | 10/1990 | Muller et al. ............ 250/584 |
| 5,260,573 A | * | 11/1993 | Tsuchino ............ 250/584 |
| 6,047,257 A | * | 4/2000 | Dewaele ............ 704/270 |
| 6,271,536 B1 | * | 8/2001 | Buytaert et al. ............ 250/584 |
| 6,340,931 B1 | * | 1/2002 | Harrison et al. ............ 340/572.1 |
| 6,350,985 B1 | * | 2/2002 | Rodricks et al. ............ 250/252.1 |
| 6,389,156 B1 | * | 5/2002 | Tsuchino et al. ............ 382/132 |
| 6,444,997 B2 | * | 9/2002 | Isoda ............ 250/587 |
| 6,934,358 B2 | * | 8/2005 | Ritt et al. ............ 378/62 |
| 6,945,713 B2 | * | 9/2005 | Vraa et al. ............ 396/511 |
| 2001/0017356 A1 | * | 8/2001 | Van Uffel ............ 250/586 |
| 2002/0071421 A1 | * | 6/2002 | Chiu et al. ............ 370/349 |
| 2003/0178590 A1 | * | 9/2003 | Yasuda et al. ............ 250/587 |
| 2005/0133745 A1 | * | 6/2005 | Haug et al. ............ 250/581 |
| 2005/0134936 A1 | * | 6/2005 | Haug et al. ............ 358/448 |

FOREIGN PATENT DOCUMENTS

| | | |
|---|---|---|
| EP | 1 031 854 A1 | 8/2000 |
| EP | 1 251 683 | 10/2002 |
| EP | 1 251 683 A1 | 10/2002 |

(Continued)

*Primary Examiner*—David P. Porta
*Assistant Examiner*—Jessica L Eley
(74) *Attorney, Agent, or Firm*—Houston Eliseeva LLP (57) ABSTRACT

The invention relates to an image carrier for the storage of X-ray information, as well as a corresponding system and method for the processing of such an image carrier. In order to improve the reliability when taking account of the sensitivity of the image carrier to X-radiation, the image carrier includes an electronic memory for the storage of calibration data of the image carrier that represent a measure of the sensitivity of the image carrier to X-radiation and can be used in a processing of image signals that are obtained on a reading of the X-ray information from the image carrier.

9 Claims, 4 Drawing Sheets

FOREIGN PATENT DOCUMENTS

| | | |
|---|---|---|
| EP | 0 727 696 | 5/2003 |
| EP | 0 727 696 B1 | 5/2003 |
| EP | 1 391 780 | 2/2004 |
| EP | 1 391 780 A1 | 2/2004 |
| EP | 03 10 4749 | 4/2004 |
| EP | 1 031 854 | 1/2005 |
| WO | WO 02 42794 | 5/2002 |
| WO | WO 02/42794 A2 | 5/2002 |

* cited by examiner

IMAGE CARRIER FOR STORING X-RAY INFORMATION, AND A SYSTEM AND METHOD FOR PROCESSING AN IMAGE CARRIER

FIELD OF THE INVENTION

The present invention relates to an image carrier for storing X-ray information, as well as to a corresponding system and method for processing such an image carrier.

BACKGROUND OF THE INVENTION

Generic image carriers are used, in particular for medical purposes, in the field of computer radiography (CR). For this, X-ray images are recorded in a storage phosphor layer by storing the X-radiation passing through an object, for example a patient, as a latent image in the storage phosphor layer. In order to read the stored X-ray information the storage phosphor layer is illuminated with stimulation light, whereby the layer is excited to emit light, which is captured by an optical detector and converted into electrical signals. The electrical signals may be processed further as necessary and displayed on a monitor or output on a corresponding output device, such as for example a printer. After an erasure procedure, in which any remaining X-ray information is completely eliminated from the storage phosphor layer, the storage phosphor layer is available for recording further X-ray photographs.

Since storage phosphor layers in general have different sensitivities to X-radiation, then inter alia the sensitivity of the respective storage phosphor layer to X-radiation must be taken into account when processing the image signals obtained on reading the image carrier. The corresponding data, that are a measure of the sensitivity of the storage phosphor layer of an image carrier to X-radiation, are according to the prior art generally supplied ex works on a separate data carrier together with the image carrier. In this connection, if there is confusion concerning the individual data carriers generally belonging to different image carriers, it may happen that the image signals obtained from a storage phosphor layer of an image carrier are mistakenly corrected with the corresponding data of another image carrier. This leads to an unacceptable falsification of the read X-ray information.

SUMMARY OF THE INVENTION

An object of the present invention is to provide an image carrier as well as a corresponding system and method for the processing of the image carrier, in which different sensitivities of the image carrier to X-radiation are taken into account with an increased degree of reliability.

The image carrier of the invention comprises an electronic memory for the storage of calibration data of the image carrier, in which the calibration data represent a measure of the sensitivity of the image carrier to X-radiation and can be used in the processing of image signals that are obtained on reading the X-ray information from the image carrier.

Due to the storage of the calibration data in the electronic memory located on the image carrier an additional transfer of the calibration data via an extra data carrier can be dispensed with. In this way confusion between individual data carriers is also excluded and the reliability when taking account of different sensitivities of the image carriers is thus raised.

The electronic memory is preferably designed as an integrated electronic circuit with a non-volatile memory, for example as a ROM, PROM, EPROM or EEPROM.

Preferably, the calibration data of the image carrier represent a measure of a locally fluctuating sensitivity of the image carrier to X-radiation over a storage phosphor layer of the image carrier. In this way not only are different sensitivities of individual image carriers taken into account, but also individually occurring variations of the sensitivity over the whole area of the storage phosphor layer of an individual image carrier can be taken into account. The accuracy of the calibration is thereby increased.

The calibration data that represent a measure of the locally fluctuating sensitivity of the image carrier to X-radiation are preferably stored in a two-dimensional data field in the electronic memory of the image carrier. In this way a simple correlation between individual regions of the storage phosphor layer and their respective sensitivity is achieved.

In a further modification it is envisaged that the calibration data of the image carrier reproduce the locally fluctuating sensitivity of the image carrier in individual regions of the image carrier, in which the individual regions correspond to the individual image points (pixels) that are obtained on reading the X-ray information stored in the image carrier. A pixel-accurate calibration is thereby made possible that takes account of locally different sensitivities with a very high degree of accuracy.

In an alternative modification it may however also be envisaged that the calibration data of the image carrier reproduce the locally fluctuating sensitivity of the image carrier in individual regions of the image carrier, in which the individual regions are larger than the individual image points (pixels) that are obtained on reading the X-ray information stored in the image carrier. In this way the storage space requirement for the calibration data in the electronic memory can be greatly reduced, and at the same time locally different sensitivities are however taken into account with a high degree of accuracy.

In a further modification of the invention the calibration data of the image carrier are stored in a calibration data group in the electronic memory of the image carrier. In this way a clear subdivision of the memory content is achieved and also a simpler access to the calibration data of the calibration data group is made possible.

In a further advantageous modification the image carrier includes an image plate for storing the X-ray information, the electronic memory preferably being applied to the image plate. A reliable allocation to the associated image plate of the calibration data stored in the electronic memory is thereby ensured.

In an execution of this variant it is envisaged that the image plate includes a carrier layer with a storage phosphor layer located on the front side of the carrier layer, and the electronic memory is applied to an edge region of the carrier layer, in particular outside the storage phosphor layer, and/or is applied to the rear side of the carrier layer opposite the front side. Damage to the memory properties of the storage phosphor layer due to the electronic memory is thereby avoided.

As a rule the image carrier includes, apart from the image plate, a cassette that can accommodate the image plate and screen it from ambient light. If the electronic memory is designed for contactless data transfer, its memory content can be read with a corresponding RF reader also from the outside of the cassette through the cassette wall.

In an alternative modification of the invention the electronic memory is applied to the cassette. In this case the cassette need not be opened and the image plate need not be removed if the electronic memory can be read only by galvanic contact.

Advantageously the calibration data are stored in compressed form in the electronic memory of the image carrier. The storage space requirement can thereby be greatly reduced in some cases. JPEG is for example suitable as data compression method.

The system according to the invention for processing an image carrier for the storage of X-ray information comprises at least one image carrier and at least one device for processing the image carrier and/or for the further processing and/or reproduction of the X-ray information stored in the image carrier, and is characterised in that the image carrier includes an electronic memory for the storage of calibration data of the image carrier that represent a measure of the sensitivity of the image carrier to X-radiation and that can be used in a processing of image signals that are obtained on reading the X-ray information from the image carrier.

In this connection a device is designed as a read-out device that can read the X-ray information stored in the image carrier and thereby generate corresponding image signals and can process the generated image signals using the calibration data of the image carrier stored in the electronic memory. The read-out device is preferably equipped with a suitable reader by means of which the calibration data of the image carrier stored in the electronic memory of the image carrier can be read. The method according to the invention for the processing of an image carrier for the storage of X-ray information is characterised in that the image carrier includes an electronic memory for the storage of calibration data of the image carrier that represent a measure of the sensitivity of the image carrier to X-radiation and can be used in a processing of image signals that are obtained in a reading of the X-ray information from the image carrier, and the calibration data are stored, after a first reading of the calibration data from the electronic memory of the image carrier, in a memory, in particular in a central memory or in a memory of a read-out device.

Preferably, in this connection the first reading of the calibration data of the image carrier from the electronic memory of the image carrier takes place in a read-out device.

On a renewed processing of the same image carrier the calibration data of this image carrier stored after the first reading are then read from the memory, in particular from the memory of the read-out device or from the central memory. The calibration data are thereby available in a shorter time for the image signal processing than in the case of a renewed reading of the two-dimensional data record from the electronic memory of the image carrier. Also, any transmission errors in reading the data record from the electronic memory may thereby be avoided.

BRIEF DESCRIPTION OF THE DRAWINGS

Further features and advantages of the invention are given in the following description of preferred embodiments and examples of application, in which reference is made to the accompanying figures in which.

DETAILED DESCRIPTION OF THE INVENTION

Figure 1:
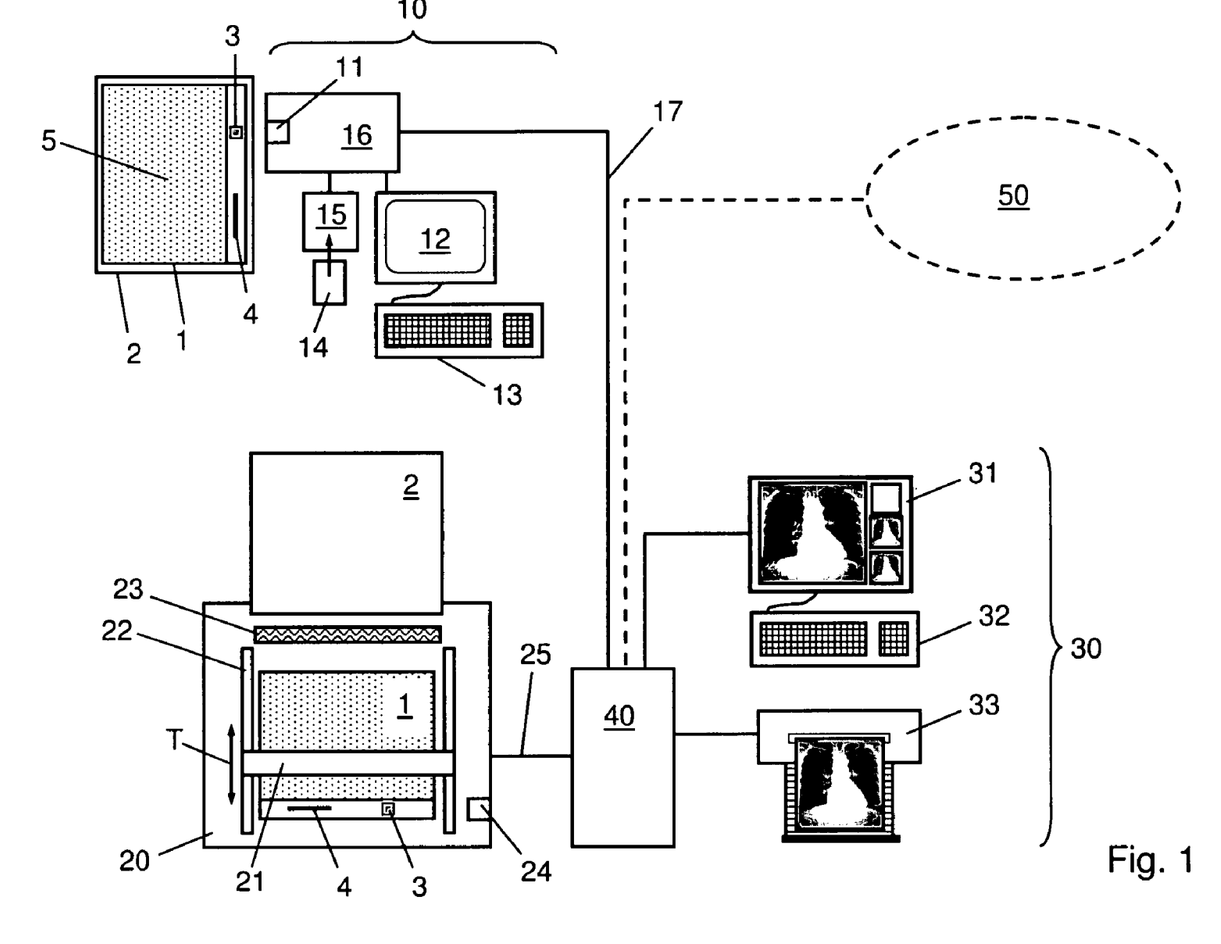
FIG. 1 shows a system for processing an image carrier for X-ray information.

FIG. 1 shows a system for processing an image carrier for X-ray information. The system comprises an identification station 10, hereinafter also referred to as ID station, a read-out device 20, a reproduction device 30 as well as a central memory 40.

The image carrier for X-ray information comprises a cassette 2 with an image plate 1 located therein. The image plate 1 comprises a carrier layer with a storage phosphor layer 5 applied thereto. The storage phosphor layer 5 preferably comprises a storage fluorescent material based on BaFBr:Eu or CsBr:Eu.

The image plate 1 is provided with an integrated circuit 3 that comprises a write-read memory, into which data can be written and from which data can be read. In order not to damage the storage function of the storage phosphor layer 5, the integrated circuit 3 is preferably arranged on the rear side or—as in the illustrated example—in the edge region of the image plate 1.

Alternatively or in addition, the integrated circuit 3 may be applied to the cassette 2. The following implementations that relate to an integrated circuit 3 located on the image plate 1 also apply as appropriate to this alternative.

After an X-ray photograph has been taken the image plate 1 located in the cassette 2, in the storage phosphor layer 5 of which plate X-ray information is stored, is brought to the ID station 10 in order to read data from the integrated circuit 3 or to write data into the integrated circuit 3. The data transfer between the integrated circuit 3 and the ID station 10 preferably takes place in a contactless manner. As a result there is no need for an exact positioning of the image plate 1 and integrated circuit 3 relative to the ID station 10, as would otherwise be necessary in a contact-affected data transfer. The contactless data transfer is preferably effected by radio frequency waves (RF waves). For this purpose the ID station 10 comprises a corresponding first write-read device 11 with an RF transmitter and an RF receiver.

The integrated circuit 3 is preferably attached, for example by adhesive, in the form of a so-called RF label, also referred to as RF tag, to the image plate 1. Such an RF tag comprises, apart from the integrated circuit 3, an antenna formed as a transponder coil. Instead of being attached as an RF tag, the integrated circuit 3 may also be attached in the form of a chip card, on the image plate 1, in which an RF tag is incorporated in a card-shaped plastic body. The chip card is preferably detachably secured to the image plate 1, for example by means of a simple socket connection in the edge region of the image plate 1. A locking mechanism, for example a snap-fit mechanism in which the chip card is locked in position by snap-type engagement, may be provided for additional securement of the chip card. This securement of the chip card on the image plate 1 is on the one hand simple and reliable, and on the other hand simplifies the replacement of the chip card by another card, which is necessary for example in the case of a defect in the integrated circuit 3.

The image plate 1 is provided with a mark 4 that can be read by the naked eye, and which represents at least a part of the data stored in the memory of the integrated circuit 3, in particular data specific to the image plate 1, and is preferably formed as an alphanumeric character sequence. In this way the data contained in the mark 4 are still accessible in the event of a defect in the integrated circuit 3 in which the data stored therein in general can no longer be read. The defective integrated circuit 3 may in this case be replaced by a new integrated circuit, into which the data contained in the mark 4 are then written. For this purpose the data of the mark 4 are read by an operator, input at the ID station 10, and finally written into the new integrated circuit. With the aid of the mark 4 it is thus ensured in a simple way that the part of the data stored in the integrated circuit 3 and contained in the mark 4 also cannot be lost in the event of a defect in the integrated circuit 3.

Alternatively or in addition a mark 4 designed in this way may also be attached to the cassette 2. The procedure to be adopted in the case of a defect in the integrated circuit is similar to that described above.

The ID station 10 comprises one or more input devices for inputting data that for example are specific to or necessary for a patient to be investigated, the read-out of the image plate 1 or the further processing of image data read from the image plate 1. In the illustrated example the input devices comprise a keyboard 13 with display unit 12, such as for example a monitor, as well as a card reader 15 for a card 14 containing data that is to be input. In particular the card 14 is a chip card, for example a medical insurance card, on which patient-specific data, such as for example the name, address, date of birth and insurance number of a patient, are stored. The card reader 15 reads these data from the card 14 and transfers them to an intermediate memory 16 of the ID station 10. Also, the data input via the keyboard 13 are transferred to the intermediate memory 16. The display unit 12 may preferably also be a so-called touch screen, in which displayed functions and/or data can be selected by touching the corresponding regions of the display.

The input data are transferred from the intermediate memory 16 to the first write-read device 11 and are written into the memory of the integrated circuit 3 on the image plate 1.

Instead of the actual input data, a reference code associated with these data may be written into the memory of the integrated circuit 3, while the input data together with the reference code associated therewith are stored in the intermediate memory 16 and/or in the central memory 40. This process is described further in more detail hereinbelow.

The cassette 2 with the image plate 1 located therein is next brought to the read-out device 20, where the cassette 2 is automatically opened and the image plate 1 is removed and inserted into the interior of the read-out device 20. In the position illustrated here the image plate 1 is already completely removed from the cassette and locked in the interior of the read-out device 20. In this position it is now read by a scanner 21 that is moved by means of a suitable transporting mechanism 22 in the transporting direction T over the image plate 1.

The scanner 21 is preferably designed as a so-called line scanner, which comprises a line-shaped stimulation light source, preferably with laser diodes arranged in a row, and a line-shaped detector, preferably a linear CCD array. During the movement of the scanner 21 over the image plate 1, this is illuminated line by line with the light from the stimulation light source, whereby emission light is excited in the storage phosphor layer 5, the intensity of the light corresponding to the X-ray information stored in the storage phosphor layer 5. The emission light is collected by the line-shaped detector and converted into corresponding image signals. Due to the continuous movement of the scanner 21 in the transporting direction T over the image plate 1, the storage phosphor layer 5 is read line by line, a two-dimensional image of the stored X-ray information thereby being obtained.

Alternatively the scanner 21 may also be designed as a so-called flying spot scanner, in which an individual laser beam is deflected by a rotating polygonal mirror onto the storage phosphor layer 5, whereby this is scanned in a punctiform manner along individual lines.

After the image plate 1 has been completely read, it is automatically re-inserted again into the cassette 2. In this connection it passes an erasure device 23 at which any remaining X-ray information in the image plate 1 is erased by illuminating the storage phosphor layer 5 with erasure radiation. The erasure device 23 comprises for this purpose a radiation source with a spectrum of broader bandwidth compared to the stimulation light source, and a suitable reflector for reflecting erasure radiation onto the storage phosphor layer 5 of the image plate 1.

The read-out device 20 comprises a second write-read device 24, by means of which data can be read from or written into the integrated circuit 3. Like the first write-read device 11 of the ID station 10, the second write-read device 24 is also preferably designed for contactless data transfer, in particular by means of RF waves. The data read from the memory of the integrated circuit 3 by means of the second write-read device 24 are used in particular for controlling the read-out of the image plate 1 with the scanner 21 and/or for controlling the erasure of the image plate 1 with the erasure device 23. In addition, data may be written into the integrated circuit 3 using the second write-read device 24 in order preferably to update data relating to the processing status of the image plate 1, for example whether the image plate 1 has already been read or erased.

During the line-by-line reading out of the image plate 1 with the scanner 21 image data are generated that represent the X-ray information stored in the image plate 1. These image data are transferred via a first data bus 25, in particular a serial data bus, such as for example a so-called FireWire (IEEE 1394), to the central memory 40 and are stored there.

The image data stored in the central memory 40 may then be processed further and/or reproduced in the reproduction device 30. For this purpose the reproduction device 30 comprises a monitor 31 that can be controlled by means of a keyboard 32. Alternatively or in addition, a hard copy device 33, for example a laser printer, may be provided for outputting the image data.

The central memory 40 may optionally be connected to a network 50, in particular to a local network (LAN). In this way it is possible for data and/or image data stored in the central memory 40 to be accessed from other systems, in particular from other ID stations and/or reproduction devices.

The central memory 40 may be designed as a separate central unit that may be integrated for example in a central file server. Alternatively the central memory 40 may also be an integral constituent of the ID station 10, of the read-out device 20 or of the reproduction device 30.

Figure 2:
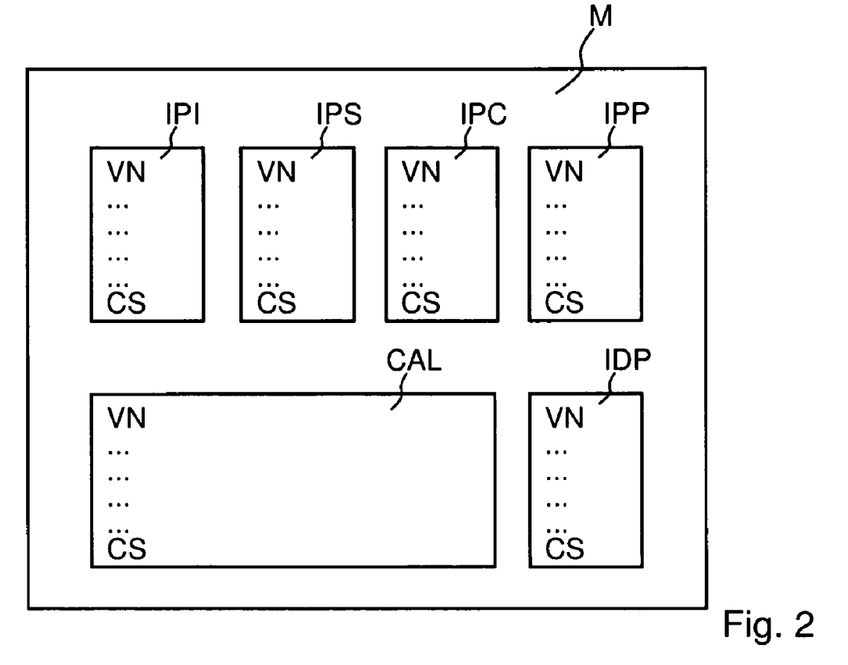
FIG. 2 is a first example of a structure of the data stored in the integrated circuit of the image carrier.

FIG. 2 shows a first example of a structure of the data stored in the memory M of the integrated circuit 3 of the image carrier. The data transfer within the system described in FIG. 1 is discussed in more detail with the aid of this structure. It should be noted that the illustration chosen here reproduces the structure of the data merely in a highly diagrammatic manner and is not restricted to a specific spatial arrangement or a specific sequence of the data in the memory M of the integrated circuit 3.

The data stored in the memory M are composed of different data groups IPI, IPS, IPC, IPP, CAL and IDP, and are filed there in each case as an ASCII string. A version number VN as well as a check sum CS are associated with each data group.

The version number VN located at the beginning of each data group indicates in which data structure the data of a data group are filed. It is thereby possible to assign different data structures to one and the same data group. This is always necessary if other or additional data are to be filed in the memory M, for example with a new type of image plate or a new type of further processing of the image data. With the aid of the version number VN of a data group the individual components of the system, e.g., the ID station 10, the read-out device 20 and the reproduction device 30 can recognise which data are contained in the respective data group and in which data length, sequence, etc., these data are present.

The check sum CS located at the end of each data group is derived from the individual data of this data group. With the aid of the respective check sum CS it can be established whether the data of this data group have been stored or read in an error-free manner. The remainder of the division of the sum $\Sigma$ of the numerical values of all bytes contained in this data group divided by 256 preferably serves as check sum CS, i.e., $$CS = \Sigma \text{modulo } 256$$

The structure and the function of the individual data groups IPI, IPS, IPC, IPP, CAL and IDP are discussed in more detail hereinafter.

An image carrier data group IPI contains specific data of the image plate 1 and/or of the cassette 2. These data are stored in the memory M during the production of the image plate 1 or cassette 2 and remain unchanged during the processing of the image plate 1 or cassette 2 at the ID station 10 and/or in the read-out device 20, i.e., the data stored in the image carrier data group IPI are read exclusively at the ID station 10 or in the read-out device 20. Apart from the version number VN and the check sum CS, the image carrier data group IPI includes the following data:

initialisation date: corresponds to the date at which the data of the image carrier data group IPI were read into the memory M of the image plate 1;

image plate serial number: serves for the unambiguous identification of the image plate 1 and is preferably composed of a code identifying the respective product charge of the image plate 1 and a consecutive number;

image plate size;

size of an area on the image plate 1 to be read;

image plate type: for example image plate based on pulverulent or acicular storage fluorescent materials, such as e.g., so-called powder IP or needle IP;

image plate sensitivity; and image plate erasure property: e.g., as a measure of the duration and/or intensity of the light emitted by an erasure device 23.

Preferably, the contents of the image carrier data group IPI are in addition applied as a visually readable mark 4 (see FIG. 1) to the image plate 1 and/or the cassette 2. This has the advantage that the data of the image carrier data group IPI specific to the image plate 1 or cassette 2 and necessary for their processing cannot be lost even if the integrated circuit 3 is defective and can no longer be read. In such a case the defective integrated circuit 3 is simply replaced by a new integrated circuit, which is then provided with the data taken from the mark 4. Such a mark 4 may for example have the following form:

301-6KBQMF0001-20030702-1-1-0-1000-1000-123

The first three digits. (301) as well as the last three digits (123) comprise the version number VN and the check sum CS. The version number VN is followed by the image plate serial number (6KBQMF0001), the initialisation date (20030702), values for the image plate size (1), the size (1) of the area of the image plate to be read, as well as the image plate type (0), the image plate sensitivity (1000) and, finally, the image plate erasure property (1000).

The data taken from the mark 4 may be written in a simple manner at the ID station 10 into the memory of the new integrated circuit, without the need for a new initialisation by the manufacturer of the image plate 1 or cassette 2. In the simplest case the data of the mark 4 are read by an operator, input via the keyboard 13 of the ID station 10, and then written into the memory of the new integrated circuit.

The visually, i.e., with the human eye, readable mark 4 described above represents a particularly simple possibility for providing additional security of data stored in the integrated circuit 3. Obviously, instead of a visually readable mark a machine-readable mark (not shown) may alternatively or additionally be provided, for example in the form of a barcode or magnetic strip. In order to input the data contained in the machine-readable mark a corresponding barcode or magnetic strip reading device is then necessary, which transfers the mechanically read-in data to the ID station 10, where the data can then be written into the new integrated circuit.

The data of a state data group IPS relate to the respective processing state of the image plate 1 or cassette 2 and are altered in the ID station 10 as well as in the read-out device 20. Apart from the version number VN and the check sum CS this data group includes the following data:

image plate status: e.g., whether the image plate 1 is already initialised (i.e., data of the image carrier data group IPI are stored in the memory M) and/or an X-ray image has already been taken, erased or is still to be erased;

image plate cycles: total number of X-ray photographs with this image plate 1. This total number is increased by the value 1 in the read-out device 20 after each read-out procedure or erasure procedure; and read-out under deflection: number of image plate cycles in which the image plate 1 is bent during the read-out procedure. This number is a measure of the level of wear and tear and/or damage of an image plate 1. This entry may be omitted for example in systems in which the image plate lies on a firm, flat substrate during the read-out and is consequently not bent.

A control data group IPC includes all specific data for an X-ray photograph that are necessary for reading the image plate 1 in the read-out device 20. The read-out device 20 in this case accesses exclusively in a reading manner the data stored in the control data group IPC. In addition to the version number VN and the check sum CS the control data group IPC includes the following data:

scanner sensitivity: specifies the sensitivity to be adjusted in the scanner 21 on reading the image plate 1 and depends on the X-ray dose in regions of the image plate 1 that contain diagnostic information;

X-ray dose: corresponds to the maximum X-ray dose during an X-ray photograph and represents a measure of the intensity of the erasure device 23 to be adjusted during erasure of the image plate 1; and operating mode: e.g., ignoring or reading X-ray information from specific edge regions of the image plate 1.

In a processing data group IPP data are stored that are necessary for a further processing of image data obtained from the X-ray information of the image plate 1. These data are accessed exclusively by the reproduction device 30, which comprises a corresponding image processor for the further processing of the image data. The read-out procedure in the read-out device 20 is not influenced by these data.

Preferably the data of the processing data group IPP are read by means of the second write-read device 24 into the readout device 20 and filed together with the image data obtained from image plate 1 in the central memory 40. The reproduction device 30 can then access in a simple way both the image data to be processed as well as the data of the processing data group IPP necessary for this purpose.

In a preferred modification it is envisaged that the data of the processing data group IPP required for the further processing of the image data be input into the ID station 10 and that unique reference codes (IPP-Ref) be allocated to these, which are then written, instead of the data for the further processing, into the memory M. The data for the further processing itself are stored together with the reference codes (IPP-Ref) in the central memory 40. The reproduction device 30, which requires the data stored in the central memory 40 for the further processing, can then access, with the aid of the reference codes (IPP-Ref) transferred with the image data from the read-out device 20, the data for the further processing stored in the central memory 40. Apart from the version number VN and the check sum CS the processing data group IPP in this case then comprises the following data:

reference code for the type of further processing to be carried out;

reference code for photograph and patient data; and unambiguous identification of the central memory to which the reference codes refer, such as for example the name of the central memory in a network.

A calibration data group CAL comprises calibration data of the image plate 1. The calibration data preferably exist as a two-dimensional data field that mirrors the different local sensitivity of the image plate 1 to X-radiation. The data of the calibration data group CAL are preferably stored together with the data of the image carrier data group IPI in the production and initialisation of the image plate 1 or cassette 2 in the memory M of the integrated circuit 3 and are not altered during the processing of the image plate 1 or cassette 2. In addition to the version number VN and the check sum CS the calibration data group CAL includes in particular the following data:

number of columns of the two-dimensional data field of the calibration data;

number of lines of the two-dimensional data field of the calibration data; and two-dimensional data field of the calibration data.

The calibration data of the image plate 1 are used in the read-out device 20 for a preliminary evaluation of the image signals obtained by means of the scanner 21 when reading the image plate 1, in order to take account of locally different sensitivities of the image plate 1 to X-radiation. To this end the calibration data are read from the integrated circuit 3 in the read-out device 20 and sent to the preliminary processing of the image signals.

Once the calibration data have been read, they are preferably stored in a memory (not shown) of the read-out device 20 or are transferred via the first data bus 25 to the central memory 40 and stored there. If this same image plate 1 with another X-ray photograph is then subjected to a read-out process in the same read-out device 20, this read-out device 20 can directly access the memory of the read-out device 20 or the central memory 40 and retrieve the calibration data of the image plate 1 necessary for the preliminary processing of the image signals. The calibration data are thus available in a shorter time for the preliminary processing than is the case with a renewed read-out of the two-dimensional data record from the integrated circuit 3. Also, any transfer errors occurring when reading the data record from the integrated circuit may thereby be avoided.

Alternatively the calibration data may already be read from the integrated circuit 3 at the ID station 10, transferred via a second data bus 17 to the central memory 40, and stored there. A read-out and transfer of the calibration data to the central memory 40 during the first read-out procedure in the read-out device 20 may then be omitted. The second data bus 17 is preferably likewise designed as a serial data bus, e.g., as an RS232 data bus.

In principle it is possible to read anew from the integrated circuit 3 the two-dimensional data field of the calibration data of the image plate 1 at each read-out procedure in the read-out device 20. In this case a permanent connection between the read-out device 20 and the central memory 40 may optionally be completely dispensed with, or at least the data flow between the individual components of the system, in particular between the read-out device 20 and central memory 40, may be kept extremely low.

In addition to the calibration data of the image plate 1, calibration data of the scanner 21 that mirror local differences in the sensitivity of the scanner 21 and that are preferably used together with the calibration data of the image plate 1 for the preliminary processing of the image signals, are also filed in the central memory 40 or in the memory of the read-out device 20. Finally, image data of the X-ray image stored in the image plate 1, from which the influence of locally different sensitivities of the image plate 1 and of the scanner 21 has been eliminated, are obtained from the preliminary processing of the image signals.

Typically the two-dimensional data field of the calibration data of the image plate 1 has between about 30 and 40 columns and between about 40 and 50 lines, the length of the respective data being in each case two bytes. The memory size to be reserved for such a two-dimensional data field that preferably has 35 columns and 43 lines is accordingly 2×35× 43=3010 bytes.

In the described example the calibration data reproduce the sensitivity of individual regions of the storage phosphor layer 5 that are larger than the individual image points (pixels) obtained in the line-by-line read-out of the image plate 1. In this way the memory space requirement for the calibration data in the integrated circuit 3 can be greatly reduced, and at the same time locally different sensitivities can be taken into account with a high degree of accuracy.

If sufficient storage space is present in the integrated circuit 3, the calibration data may however also reproduce the sensitivity of the image plate 1 in individual regions of the image plate that correspond to the individual image points. In this way a calibration accurate in terms of pixels is possible that takes into account with an even higher degree of accuracy locally different sensitivities.

In order to occupy as little storage space as possible in the memory M of the integrated circuit 3, the calibration data of the image plate 1 are advantageously subjected to a compression process before the data are filed in the integrated circuit 3. Data that are specific to a patient to be investigated are stored in a patient data group IDP. In addition to the version number VN and the check sum CS, the patient data group IDP includes for example the following data:

patient's name;

patient's date of birth; and patient's gender.

Preferably, instead of or in addition to the aforementioned patient-specific data of the patient data group IDP, a reference code IDP-Ref that constitutes a reference to the data of the patient data group IDP that are filed in the central memory 40 is written into the memory M. The reference code IDP-Ref, which is also referred to as the patient identification code and allows the patient to be identified unambiguously, is written with the first write-read device 11 of the ID station 10 into the memory M of the integrated circuit 3 and is stored together with the data of the patient data group IDP in the intermediate memory 16 of the ID station 10 and/or in the central memory 40.

With the aid of the patient identification code IDP-Ref, patient-specific data stored in the intermediate memory 16 or central memory 40 can then be accessed. The patient identification code IDP-Ref is for this purpose read from the integrated circuit 3 either in the ID station 10 or in the read-out device 20 and transferred to the reproduction device 30 or transferred together with the image data read from the image plate 1 to the reproduction device 30, which latter device can then access, with the aid of the patient identification code IDP-Ref, the corresponding patient-specific data in the intermediate memory 16 or central memory 40.

In principle the patient data group IDP may however also be omitted if, as already described above, reference codes for patient data are already provided in the processing data group IPP that refer inter alia to the corresponding patient data, such as for example name and/or date of birth and/or gender of the patient, in the central memory 40.

Figure 3:
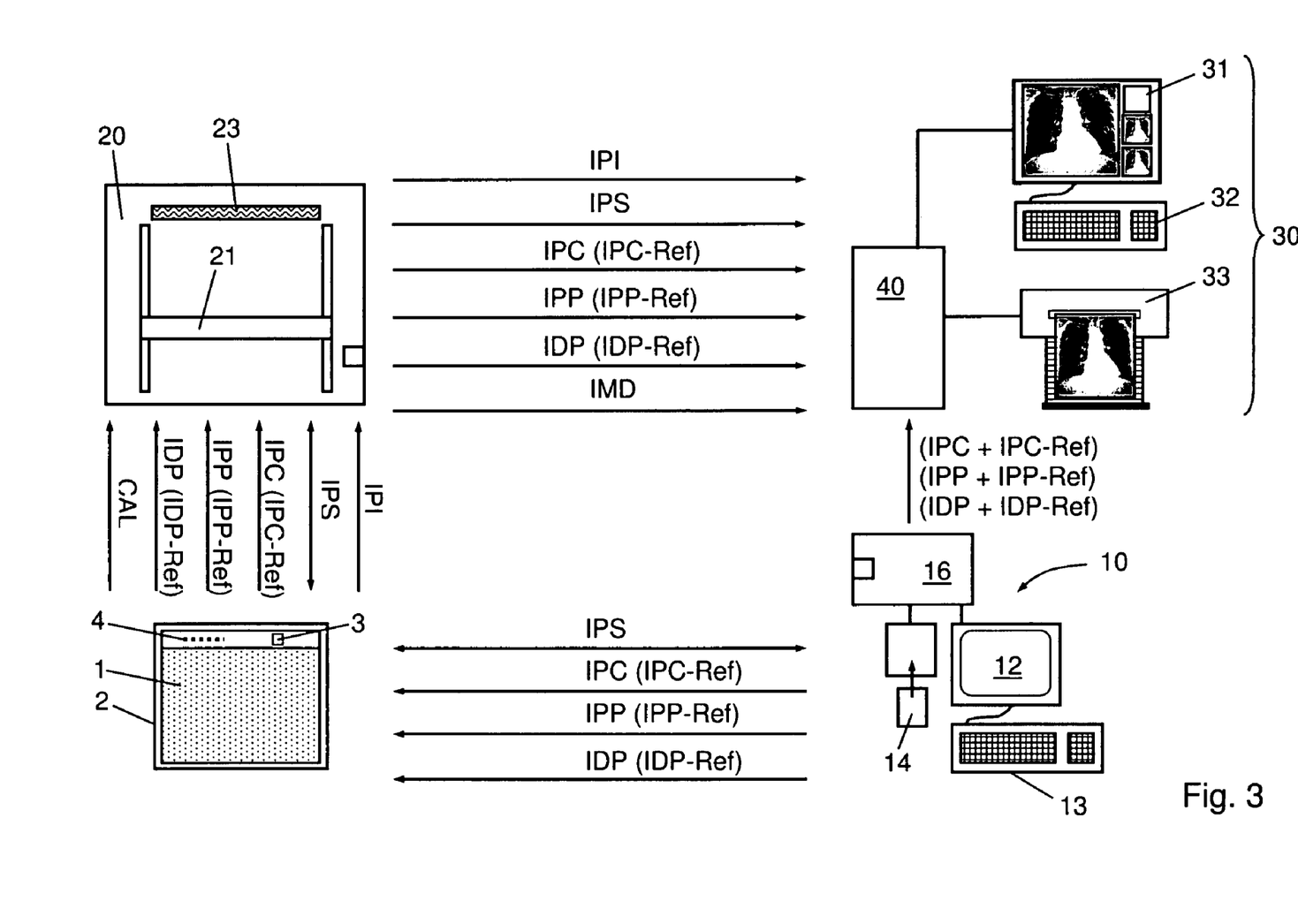
FIG. 3 is a diagrammatic representation of a first variant of the data flow between individual components of the system illustrated in FIG. 1.

FIG. 3 shows diagrammatically a first variant of the data flow between the individual components of the system according to the invention illustrated in FIG. 1. The data flow is discussed in more detail hereinafter with the aid of a complete radiography procedure.

Immediately after an X-ray photograph of a patient has been taken the cassette 2 together with the image plate 1 located therein is brought to the ID station 10. At the ID station 10 the following steps are executed:

a) Reading of data of the state data group IPS relating to the processing status of the image plate 1 from the memory M of the integrated circuit 3. Checking whether the processing status is set to "image plate initialised" or "image plate erased". If the image plate 1 has not been initialised or erased, the operator must choose between two alternatives, namely to overwrite the data or to terminate the processing.

b) Input of patient-specific data of the patient data group IDP by means of the keyboard 13 and/or display unit 12 and/or card 14.

c) Input by means of the keyboard 13 and/or display unit 12 of data of the control data group IPC necessary for the read-out of the image plate 1 in the read-out device 20.

d) Input by means of the keyboard 13 and/or display unit 12 of data of the processing data group IPP necessary for the further processing of image data in the reproduction device 30.

e) Writing of the input data of the control, processing and patient data group IPC, IPP and IDP into the memory M of the integrated circuit 3 of the image plate 1 or cassette 2.

f) Writing of data of the state data group IPS relating to the current processing status into the memory M: processing status is set to "X-ray picture taken."

The cassette 2 together with the image plate 1 located therein is then brought to the read-out device 20. There the image plate 1 is read line-by-line with the scanner 21, image signals thereby being generated that correspond to the X-ray information stored in the image plate 1. The image signals are subjected to a preliminary processing in which image data IMD are obtained that can be passed on to the reproduction device 30. In the read-out device 20 the following steps in particular are carried out:

a) Reading of data of the image carrier, state, control, processing and patient data group IPI, IPS, IPC, IPP and IDP from the memory M.

b) Reading of data of the calibration data group CAL, i.e., calibration data of the image plate 1, from the memory M.

Or:

reading of data of the calibration data group CAL already stored during a previous read-out procedure of this image plate 1 in a memory (not shown) of the read-out device 20.

c) Checking of the read data of the state data group IPS to see whether the processing status of the image plate 1 is set to "X-ray picture taken." If not, the further processing is discontinued.

d) Reading of calibration data (CALS) of the scanner 21 stored in a memory of the read-out device 20.

e) Line-by-line reading with the scanner 21 of the X-ray information stored in the image plate 1, including data of the image carrier and control data group IPI and IPC, and generation of corresponding image signals.

f) Preliminary processing of the generated image signals with the aid of the calibration data CAL of the image plate 1 and the calibration data (CALS) of the scanner 21 relating to image data IMD.

g) Erasure of any remaining X-ray information in the image plate 1 using the erasure device 23, including data of the image carrier and control data group IPI and IPC.

h) Storage of the image data IMD together with the data of the processing and patient data group IPP and IDP in the central memory 40.

i) Writing of data of the state data group IPS relating to the current processing status of the image plate 1 into the memory M: "image plate read" or "image plate erased."

Optionally, in step h) the data of the image carrier and/or control data group IPI and/or IPC may additionally be stored together with the image data IMD in the central memory 40.

The image data IMD generated on reading the image plate 1 may then be shown on a monitor 31 in the reproduction device 30 and/or may be output at a hard copy device 33. In detail the following steps are carried out in this connection:

a) Reading of the image data IMD and associated data of the processing and patient data group IPP and IDP from the central memory 40.

b) Further processing of the image data IMD on the basis of the data of the processing data group IPP.

c) Reproduction—e.g., on the monitor 31 and/or hard copy device 33—of the further processed image data IMD, including the data of the processing and/or patient data group IPP and/or IDP.

In a modification of the data flow illustrated in FIG. 3, at the ID station 10 instead of the data relating to the control, processing and patient data group IPC, IPP and IDP one or more reference codes IPC-Ref, IPP-Ref and IDP-Ref are written into the memory M of the integrated circuit 3 of the image plate 1 or cassette 2. The reference codes IPC-Ref, IPP-Ref and IDP-Ref are stored together with the corresponding data of the control, processing and patient data group IPC, IPP and ICP in the central memory 40. With the aid of the reference codes IPC-Ref, IPP-Ref and IDP-Ref the read-out device 20 can then access the data of the corresponding data group IPC, IPP and IDP stored in the central memory 40. The reference codes IPC-Ref, IPP-Ref and IDP-Ref transferred in this modification, optionally together with the associated data of the corresponding data group IPC, IPP and IDP, are shown in round brackets ( ) in FIG. 3. For the rest, the comments made above apply as appropriate.

Figure 4:
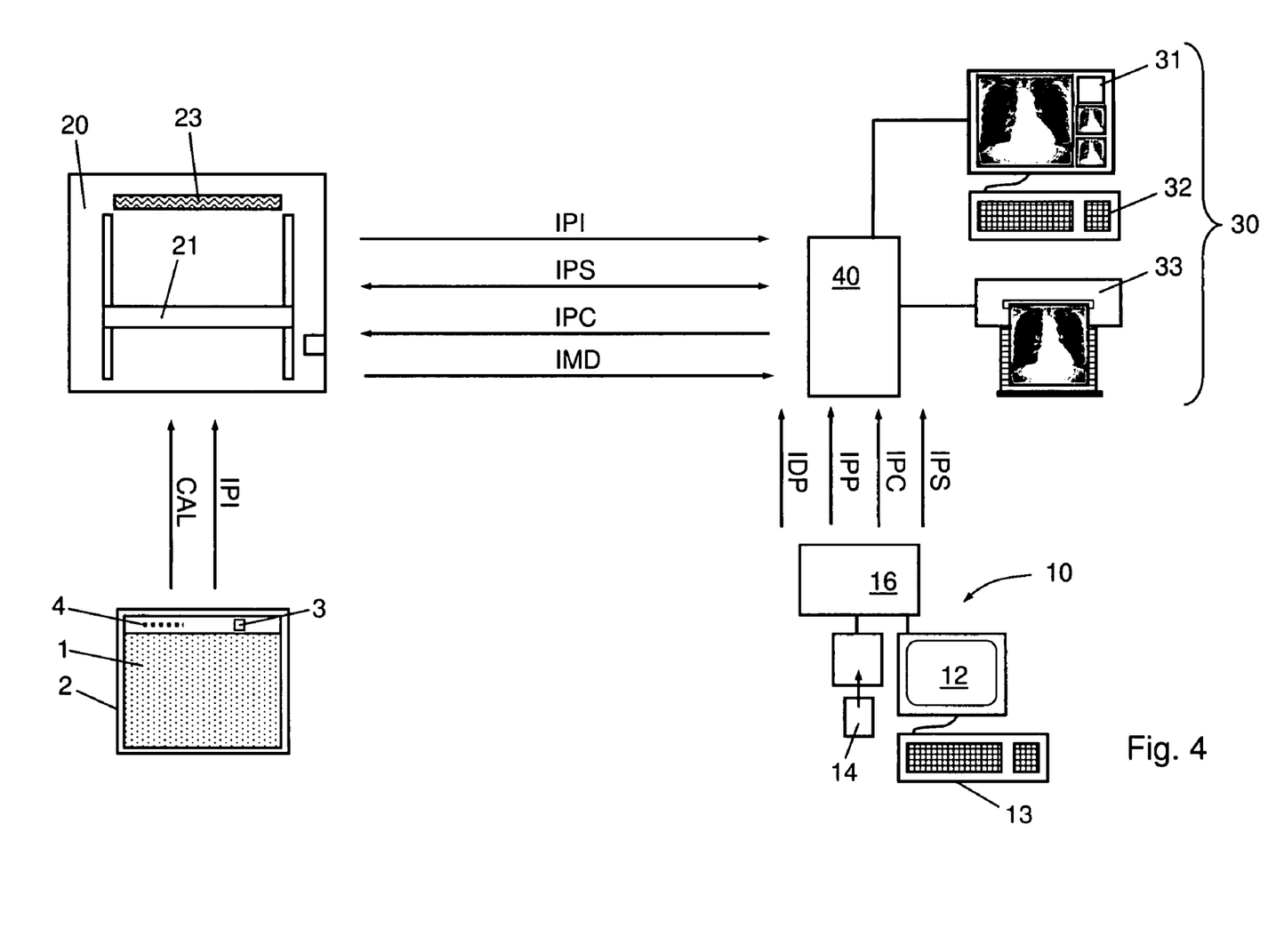
FIG. 4 is a diagrammatic representation of a second variant of the data flow between individual components of the system illustrated in FIG. 1.

FIG. 4. shows diagrammatically a second variant of the data flow between the individual components of the system illustrated in FIG. 1. In this variant of the data flow, data of the state, control, processing and patient data group IPS, IPC, IPP and IDP are input at the ID station 10—as described in detail hereinbefore—but are not written into the memory M of the integrated circuit 3 located on the image plate 1 but are instead transferred to the central memory 40 and stored there. In this variant only data of the image carrier and calibration data group IPI and CAL are stored in the memory M of the integrated circuit 3. Correspondingly, in the read-out device 20 only data of the image carrier and calibration data group IPI and CAL, which include image plate-specific data and the calibration data of the image plate 1, are read from the integrated circuit 3. The data of the state data group IPS relating to the processing status of the image plate 1 and also the data of the control data group IPC necessary for the reading of the X-ray information from the image plate 1 as well as the subsequent erasure of residual image information are on the other hand read from the central memory 40. For the rest, the comments regarding FIG. 3 apply as appropriate.

In the image plates 1 illustrated in the examples of FIGS. 3 and 4 the mark 4, which represents a part of the data, in particular data of the image carrier data group IPI, stored in the memory M of the integrated circuit 3, is applied to the rear side of the carrier layer of the image plate 1. The mark 4 is therefore shown by a dotted line.

Figure 5:
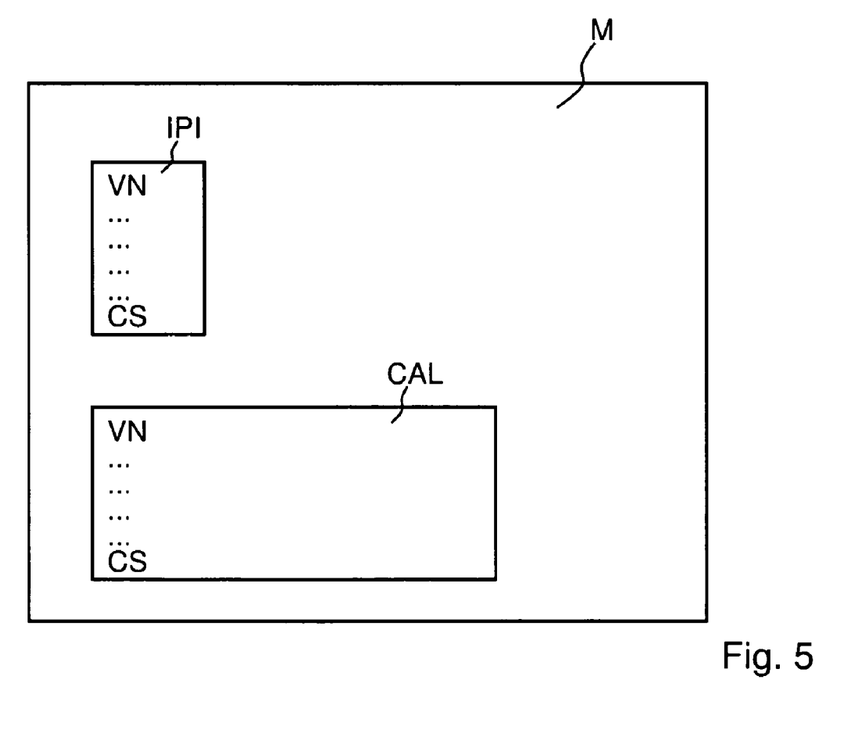
FIG. 5 is a second example of a structure of the data stored in the integrated circuit of the image carrier.

FIG. 5 shows a second example of a structure of the data stored in the integrated circuit 3 of the image carrier, in the variant of the data flow illustrated in FIG. 4. As already discussed, with this variant only data of the image carrier and calibration data group IPI and CAL are stored in the memory M. The above comments regarding FIG. 2 apply as appropriate to the structure and the contents of the individual data groups IPI and CAL.

In this variant the memory space requirement in the memory M of the integrated circuit can be reduced compared to the example shown in FIGS. 2 and 3.

In the example shown in FIGS. 2 and 3 on the other hand more memory space is required, although however the read-out device 20 can extract the data necessary for the reading or erasure directly from the memory M of the integrated circuit 3 on the image plate, and the central memory 40 does not have to be accessed for this purpose. An independence of the read-out device 20 from a central memory 40 is thereby achieved.

The invention claimed is:

1. A method for the processing of an image carrier for the storage of X-ray information, comprising:
   providing the image carrier with an electronic memory for the storage of calibration data of the image carrier that represent a measure of a sensitivity of the image carrier to X-ray radiation;
   accessing and using the calibration data from the electronic memory of the image carrier in a processing of image signals that are obtained on reading the X-ray information of a first X-ray photograph from the image carrier by a read-out device during a first reading of the image carrier;
   storing the calibration data, after a reading of the calibration data from the electronic memory of the image carrier by the read-out device, so that the calibration data continue to be stored both in the electronic memory of the image carrier and also in a central memory or in a memory of the read-out device after the image carrier has been used to store new X-ray information of new X-ray photographs and prior to subsequent readings of the new X-ray information by the read-out device; and
   during subsequent readings of new X-ray information from the same image carrier by the read-out device, using the calibration data of this image carrier that are stored in the central memory or in the memory of the read-out device, which were accessed and stored from the first reading of the image carrier, in a new processing of image signals that are obtained in the subsequent readings of the new X-ray information from the image carrier.

2. A method as claimed in claim 1, wherein the calibration data are stored in compressed form in the electronic memory of the image carrier.

3. A method as claimed in claim 1, wherein the step of using the calibration data comprises using the calibration data to compensate for a locally fluctuating sensitivity of the image carrier to X-ray radiation over a storage phosphor layer of the image carrier.

4. A method as claimed in claim 1, further comprising storing the calibration data in the electronic memory of the image carrier in a two-dimensional data field.

5. A method as claimed in claim 1, wherein the step of using the calibration data comprises using the calibration data to compensate for locally fluctuating sensitivity of the image carrier in individual regions of the image carrier, in which the individual regions correspond to individual image points that are obtained on a reading of the X-ray information stored in the image carrier.

6. A method as claimed in claim 1, wherein the step of using the calibration data comprises using the calibration data to compensate for locally fluctuating sensitivity of the image carrier in individual regions of the image carrier, in which the individual regions are larger than individual image points that are obtained on a reading of the X-ray information stored in the image carrier.

7. A method as claimed in claim 1, further comprising storing the calibration data of the image carrier in a calibration data group in the electronic memory of the image carrier.

8. A method as claimed in claim 7, further comprising including a version number with the calibration data group that characterizes a structure in which the data of the calibration data group exist.

9. A method as claimed in claim 7, further comprising including a check sum with the calibration data group that is derived from the data of the calibration data group to check whether the data of the calibration data group have been stored and/or read in an error-free manner.

* * * * *